(12) United States Patent
Boschetti et al.

(10) Patent No.: US 7,659,393 B2
(45) Date of Patent: Feb. 9, 2010

(54) METHOD OF PREPARING CIS-8B-METHYLDECAHYDRO-2A,4A,6A,8A-TETRAAZACYCLOPENTA[FG]ACENAPH-THYLENE, CIS-DECAHYDRO-2A,4A,6A,8A-TETRAAZA CYCLOPENTA[FG]ACENAPH-THYLENE, CYCLENE AND FUNCTIONALISED CYCLENES

(75) Inventors: Frederic Boschetti, Dijon (FR); Fanny Chaux, Dijon (FR); Franck Denat, Dijon (FR); Roger Guilard, Fontaine-les-Dijon (FR); Henry Ledon, Versailles (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 0 days.

(21) Appl. No.: 10/560,162

(22) PCT Filed: Jun. 4, 2004

(86) PCT No.: PCT/FR2004/050213

§ 371 (c)(1),
(2), (4) Date: Mar. 17, 2006

(87) PCT Pub. No.: WO2005/000823

PCT Pub. Date: Jan. 6, 2005

(65) Prior Publication Data

US 2006/0217548 A1    Sep. 28, 2006

(30) Foreign Application Priority Data

Jun. 13, 2003    (FR) .................................. 03 50217

(51) Int. Cl.
    *C07D 245/00* (2006.01)
(52) U.S. Cl. ..................................... 540/470
(58) Field of Classification Search .................. None
    See application file for complete search history.

(56) References Cited

FOREIGN PATENT DOCUMENTS

| WO | WO 96/28432 | * | 9/1996 |
|----|-------------|---|--------|
| WO | WO/97/49691 |   | 12/1997 |
| WO | WO/00/32601 |   | 6/2000 |
| WO | WO/02/06287 |   | 1/2002 |
| WO | WO 02/059122 | * | 8/2002 |
| WO | WO/03/029228 |   | 4/2003 |

OTHER PUBLICATIONS

Boschetti et al. Chemical Communications, 2002, 312-313, available online Jan. 18, 2002.*
Sandines; Rolf Wiggo et al: "A simple synthesis of the macrocycle 1,4,7,10-tetraazacyclododecane" ACTA Chemica Scandinavica, 53(12), 1402-1404, 1998, XP009025163 cited in the application p. 1403.
Herve, Gwenaelle et al: "A new route to cyclen, cyclam and homocyclen" Tetrahedron Letters, 39(38), 6861-6864, 1998, XP004132624 cited in the application p. 6863.
Hubin, Timothy J. et al: ":Synthesis and S-ray Crystal Structure Determination of the First Copper (II) Complexes of Tetraazamacrocycle-Glyoxal Condensates" Inorganic Chemistry, 41(26) 7006-7014, 2002, XP002269063 p. 7011.

* cited by examiner

*Primary Examiner*—James O Wilson
*Assistant Examiner*—Noble Jarrell
(74) *Attorney, Agent, or Firm*—Young & Thompson

(57) ABSTRACT

A method of preparing cyclene having formula (I) from triethylenetetraamine having formula (VIII) or ethylenediamine having formula (VIII') includes a series of steps. The first series of steps (I) includes a step A (one-pot preparation of the compound having formula (IIa) from the compound having formula (VIII)), followed by a step B (transforming the compound having formula (IIa) into cyclene having formula (I)). The second series of steps (II) includes a step C (preparing the compound having formula (IIb) from the compound having formula (VIII)), followed by a step D (transforming the compound having formula (IIb) into cylcene having formula (I)). The third series of steps (III) includes a step E involving the onepot preparation of the compound having formula (IIa) from the compound having formula (VIII), followed by a step B involving the transformation of the compound having formula (IIa) into cyclene having formula (I).

5 Claims, No Drawings

METHOD OF PREPARING CIS-8B-METHYLDECAHYDRO-2A,4A,6A,8A-TETRAAZACYCLOPENTA[FG]ACENAPHTHYLENE, CIS-DECAHYDRO-2A,4A,6A,8A-TETRAAZACYCLOPENTA[FG]ACENAPHTHYLENE, CYCLENE AND FUNCTIONALISED CYCLENES

The invention relates to a novel synthesis for poly-nitrogenated cycles and to some of these cycles.

Among cyclic polyamines, cyclene, or 1,4,7,10-tetraazacyclododecane, is one of the most thoroughly investigated compound, since it is the starting product for the synthesis of numerous complexes used in luminescent probes, as vectors for radioelements in radioimmunotherapy or alternatively as contrast media in medical imaging. In this latter application, complexes of gadolinium(III) with a cyclene ligand polyfunctionalized with carboxylate arms are very widely used. The best known products in Europe are Dotarem™ sold by Guerbet, ProHance™ sold by Bracco, and Gadovist™ sold by Schering.

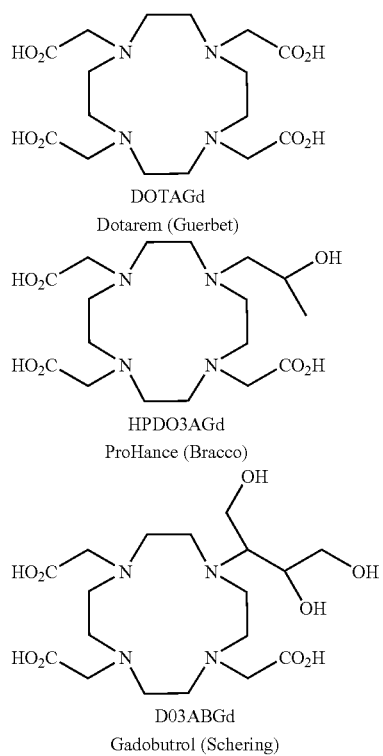

DOTAGd
Dotarem (Guerbet)

HPDO3AGd
ProHance (Bracco)

D03ABGd
Gadobutrol (Schering)

The economic worth of these systems has logically encouraged much upstream research work in order to develop novel synthetic pathways for these ligands and this research has given rise to numerous scientific publications and patent applications which are listed as references 1 to 39 at the end of the instant description.

While Dotarem™, which is a complex of gadolinium(III) or Gd(III) and 1,4,7,10-tetraazacyclododecane-1,4,7,10-tetraacetic acid, or DOTA, is prepared in a single step from cyclene, the other complexes having different functional groups, in contrast, are prepared by more delicate synthetic methods which entail the development of methods for selectively functionalizing the macrocycle.

Now, the methods which have hitherto been used are unsatisfactory, in that they either involve the use of a large excess of macrocycles in order to minimize unwanted polysubstituted products, or in that they include successive sequences of protection and then deprotection of the reactive sites.

The most effective methods for preparing cyclene are variants performed in accordance with the following scheme:

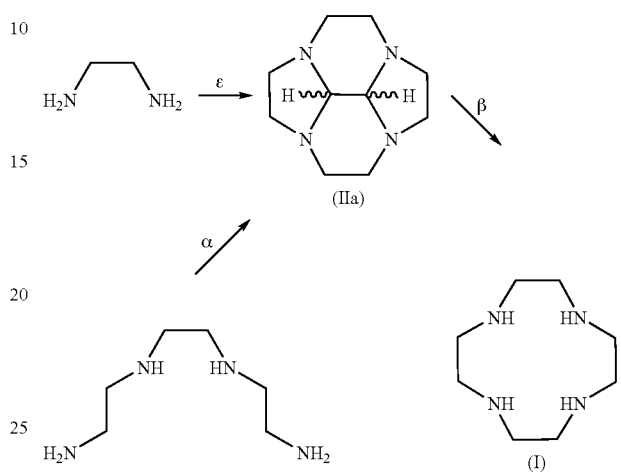

Step α:
According to reference 1: 1. $(MeO)_2CHNMe_2$ (30 min at reflux); 2. $BrCH_2CH_2Br$, $Na_2CO_3$, MeCN (3 h at reflux); 3. $H_2O_2$, water; 4. $NaBH_4$ (excess) in EtOH; Overall yield: 52%;

According to references 2 and 9: 1. glyoxal, EtOH (12 h at ambient temperature); 2. $BrCH_2CH_2Br$, DMF (20 h at ambient temperature); Overall yields: 70% (reference 2) and 28% (reference 9);

According to references 4, 6 and 12: 1. glyoxal, $Ca(OH)_2$, water (2 h at 5° C.); 2. $ClCH_2CH_2Cl$ or $BrCH_2CH_2Br$ or $ClCH_2CH_2Cl$+NaBr, $Na_2CO_3$, DMAC (48 h at 50° C.); (+$H_3PO_4$/water in reference 12); Overall yields: 33% (reference 4), 62% (reference 6) and 58% (reference 12);

According to reference 17: 1. glyoxal, $Ca(OH)_2$, water; 2. $(CO_2Et)_2$, EtOH, presence or absence of 2-hydroxypyridine or sodium methanoate or alternatively ethyl chloroacetate in the presence of $Na_2CO_3$ and NaI in EtOH; 3. reducing agent: Red-Al or vitride, toluene (112° C.); various procedures for steps 2 and 3; Overall yield: 50% maximum;

Step β:
According to reference 2: 10 eq. $NH_2OH$, EtOH (16 h at reflux); Yield: 80%;

According to reference 4: $Br_2$ or $KMnO_4$ or NaOCl then $H_2O$/NaOH (150° C. to 180° C. in an autoclave); Yield: 38 to 68%; or alternatively 50% $H_2SO_4$ (24 h at 112° C.); Yield: 22%;

According to the reference 13: 3 eq. $Br_2$ then $H_2O$/NaOH (36 h at reflux); Yield=65%; According to reference 12: diethylenetriamine, water/HCl (24 h at reflux) then successive treatments with HCl; Yield: 36%;

Step ε:
According to reference 13: 1. 0.17 eq. glyoxal, EtOH (30 min refluxing); 2. 6 eq. $ClCH_2CH_2Cl$, $Na_2CO_3$, DMAC (24 h at 70° C.); Overall yield: 60%.

According to a first aspect, the invention provides a method of preparing the cyclene of the formula (I):

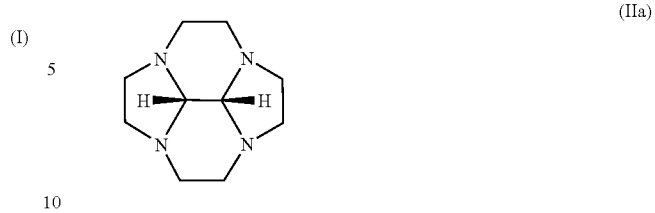

(I)

from triethylenetetraamine of the formula (VIII):

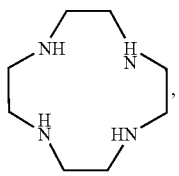

(VIII)

or ethylenediamine of the formula (VIII'):

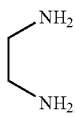

(VIII')

characterized in that said process comprises one or the other of the following series of successive steps:

series of steps (I), comprising a step (A) of a one pot preparation of the compound of the formula (IIa):

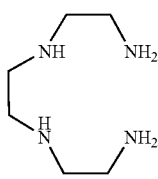

(IIa)

from the compound of the formula (VIII) as previously defined, followed by a step (B) of transformation of the compound of the formula (IIa) into the cyclene of the formula (I);

series of steps (II), made up of a step (C) of preparation of the compound of the formula (IIb):

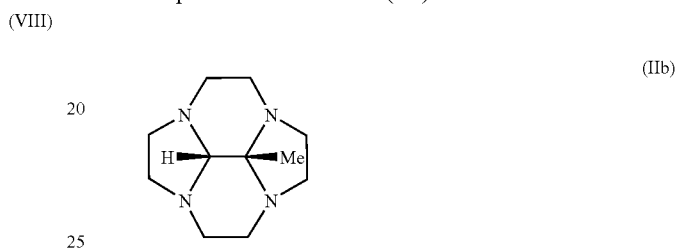

(IIb)

from the compound of the formula (VIII) as previously defined, followed by a step (D) of transformation of the compound of the formula (IIa) into the cyclene of the formula (I); or series of steps (III), comprising a step (E) of preparation in one pot of the compound of the formula (IIa) as previously defined, from the compound of the formula (VIII') as previously defined, followed by a step (B) of transformation of the compound of the formula (IIa) into the cyclene of the formula (I).

The experimental conditions appropriate for the preparation of the cyclene from the triethylenetetraamine of the formula (VIII) or the ethylenediamine of the formula (VIII'), via one of the two "bisaminal" intermediates of the formula (IIa) or of the formula (IIb), are listed beneath the following scheme:

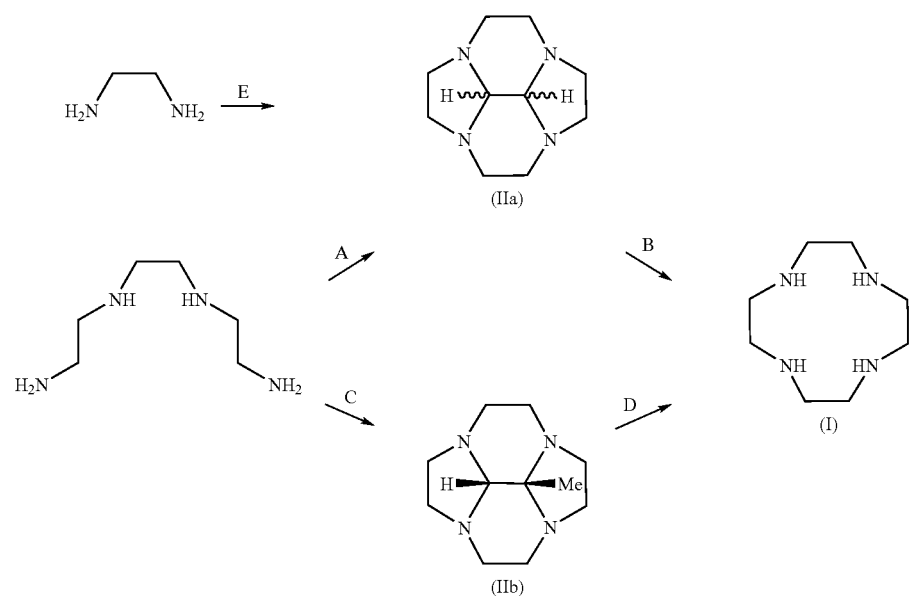

Step A:
2 equivalents of glyoxal, 2 equivalents of benzotriazole, water/MeOH (4 h at ambient temperature), then NaBH₄ (2 h at ambient temperature); Yield: 68%.

Step B:
10 equivalents of NH₂OH, EtOH (16 h at reflux) or

Br₂ or KMnO₄ or NaOCl then H₂O/NaOH (150° C. to 180° C. in an autoclave) or

Br₂ or KMnO₄ or NaOCl then 50% strength H₂SO₄ (24 h at 112° C.) or 3 equivalents of Br₂ then H₂O/NaOH (36 h at reflux) or Diethylenetriamine, water/HCl (24 h at reflux) then successive treatments with HCl.

Step C:
Pyruvaldehyde, water (2 h at 2° C.) then glyoxal, 2 equivalents of benzotriazole, water/MeOH (2 h at ambient temperature), then NaBH₄ (2 h at ambient temperature) or Pyruvaldehyde, water (2 h at 2° C.) then glyoxal, 2 equivalents of benzotriazole, water/EtOH (2 h at ambient temperature), then NaBH₄ (0° C. then 2 h at ambient temperature) or Pyruvaldehyde, EtOH (2 h at 0° C.) then glyoxal, 2 equivalents of benzotriazole, water/EtOH (2 h at ambient temperature), then NaBH₄ (0° C. then 2 h at ambient temperature) or Pyruvaldehyde, water (2 h at 2° C.) then BrCH₂CH₂Br, K₂CO₃, MeCN (48 h at 60° C.).

Step D:
37% HCl (12 h at reflux).

Step E:
0.5 equivalents of glyoxal, water (1 h at 2° C.) then 1 equivalent of glyoxal, 4 equivalents of benzotriazole, water/MeOH (2 h at ambient temperature) then NaBH₄ (2 h at ambient temperature).

According to one variant of the method as defined above, series of steps (II) comprises a step (C₁) of preparation of the compound of the formula (III):

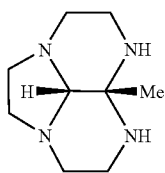

(III)

from the compound of the formula (VIII) as previously defined, followed by a step (C₂) of transformation of the compound of the formula (III) into a compound of the formula (IIb) as previously defined, followed by a step (D) of transformation of the compound of the formula (IIb) into the cyclene of the formula (I).

According to another variant of the method as defined above, series of steps (II) is performed in one pot According to a second aspect of the present invention, the invention provides the compound of the formula (IIb) as previously defined.

According to a third aspect of the present invention, the invention provides a method of preparing N-mono-functionalized cyclene derivatives of the formula (Va):

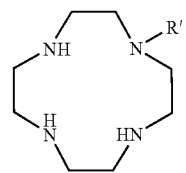

(Va)

and N₁,N₇-difunctionalized cyclene derivatives of the formula (Vb):

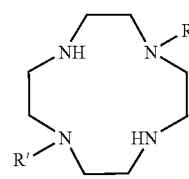

(Vb)

in which formulae (Va) and (Vb) R' represents:
- a linear or branched alkyl residue comprising from 1 to 15 carbon atoms, or
- a —(CH₂)$_w$—Y residue, in which w represents a number greater than zero and less than or equal to 6 and more particularly less than or equal to 3, and
- either Y represents an aromatic cycle comprising from 6 to 14 carbon atoms, optionally substituted in ortho and/or meta and/or para position(s) or alternatively by a halogen atom or alternatively by an alkyl group comprising from 1 to 4 carbon atoms or alternatively by an OH residue or alternatively by an OR¹ residue in which R¹ represents an alkyl residue comprising from 1 to 4 carbon atoms, an aryl residue or an aromatic heterocycle or alternatively by a nitro group or alternatively by an NH₂, —(C=O)NH₂, NHR², —(C=O)NHR², NR²R³ or —(C=O)NR²R³ group, in which R² and R³, identical or different, mutually independently represent an alkyl residue selected from among methyl, ethyl, propyl, isopropyl, n-butyl, isobutyl, sec-butyl or tert-butyl residues,
- or Y represents an aromatic heterocycle and more particularly a heterocycle comprising from one to 3 nitrogen atoms, from 4 to 12 carbon atoms, optionally substituted in ortho and/or meta and/or para position(s) or alternatively by a halogen atom or alternatively by an alkyl group comprising from 1 to 4 carbon atoms or alternatively by an OH residue or alternatively by an OR¹ residue in which R¹ represents an alkyl residue comprising from 1 to 4 carbon atoms, an aryl residue or an aromatic heterocycle or alternatively by a nitro group or alternatively by an NH₂, —(C=O)NH₂, NHR², —(C=O)NHR², NR²R³ or —(C=O)NR²R³ group, in which R² and R³, identical or different, mutually independently represent an alkyl residue selected from among methyl, ethyl, propyl, isopropyl, n-butyl, isobutyl, sec-butyl or tert-butyl residues,
- or Y represents a residue selected from among cyano, PO₃H₂, SO₃H, NH₂, —(C=O)NH₂, NHR², —(C=O)NHR², NR²R³ or —(C=O)NR²R³ residues, in which R² and R³, identical or different, mutually independently represent an alkyl residue selected from among methyl, ethyl, propyl, isopropyl, n-butyl, isobutyl, sec-butyl or tert-butyl residues or a $CO_2R^4$ residue, in which $R^4$ represents a hydrogen atom, an alkyl residue comprising from 1 to 4 carbon atoms or an aryl residue and more particularly a phenyl residue, characterized in that the compound of the formula (IX):

(IX)

in which X represents a halogen atom and $R^1$ is as previously defined, is reacted with the compound of the formula (IIb) as previously defined to give rise, depending on the stoichiometry of the reaction, either to the mixture of compounds of the formulae (IVa):

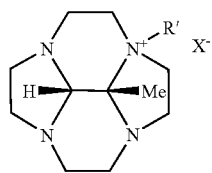
(IVa)

and (IV'a):

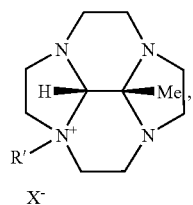
(IV'a)

or to the compound of the formula (IVb):

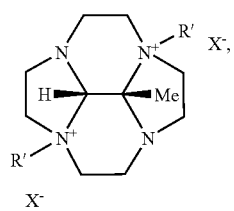
(IVb)

and in that said compounds of the formulae (IVa), (IV'a) or said compound of the formula (IVb), are subjected to alkaline hydrolysis to give rise respectively to the compound of the formula (Va) or (Vb).

According to a fourth aspect of the present invention, the invention provides a method of preparing compounds of the formula (VI):

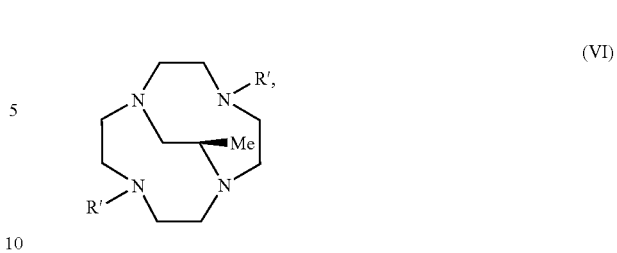
(VI)

in which R' is as previously defined, by reduction of the compound of the formula (IVb).

According to a fifth aspect of the present invention, the invention provides a method of preparing compounds of the formula (VII):

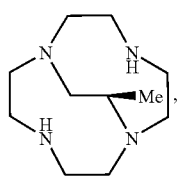
(VII)

by hydrogenolysis of the compound of the formula (VI) as previously defined.

According to a final aspect, the invention provides the compounds of the formulae (IVa), (IV'a), (IVb), (VI) and (VII).

The following Examples illustrate the invention, without limitation.

EXAMPLE 1

Synthesis of decahydro-2a,4a,6a,8a-tetraazacyclopenta[fg]acenaphthylene [compound of the formula (IIa): ceries of cteps (I), ctep (A)]

A solution of 19.86 g (136.7 mmol) of glyoxal (40% in water) in 80 ml of methanol is added by slow dropwise addition into a solution of 10.00 g (68.4 mmol) of triethylenetetraamine and 16.30 g (136.7 mmol) of benzotriazole (BtH) in 200 ml of distilled water cooled to 2° C. On completion of the addition, the mixture is adjusted to ambient temperature and is stirred for 4 h. 5.18 g (136.7 mmol) of sodium borohydride ($NaBH_4$) are then added in small portions. After 2 h of stirring at ambient temperature, the methanol is evaporated and 13 g of potassium hydroxide (KOH) pellets are added. The solution is then extracted with three 400 ml portions of chloroform. After drying over magnesium sulfate (MgSO$_4$) and evaporation of the solvents, the compound (IIa) is isolated in the form of a yellow oil which crystallizes (9.00 g; yield=68%).

$^{13}$C NMR (125 MHz, CDCl$_3$, δ in ppm): 50.9; 51.7; 78.1.

EXAMPLE 2

Synthesis of decahydro-2a,4a,6a,8a-tetraazacyclopenta[fg]acenaphthylene [compound of the formula (IIa); series of steps (III), step (E)]

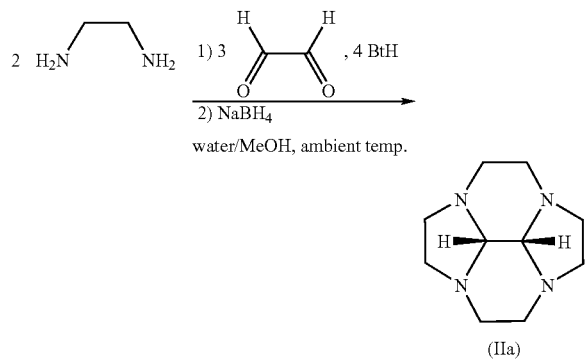

A solution of 0.99 g (6.8 mmol) of glyoxal (40% in water) in 5 ml of water is added by slow dropwise addition to a solution of 0.82 g (13.6 mmol) of ethylenediamine in 20 ml of distilled water cooled to 2° C. On completion of addition, the mixture is adjusted to ambient temperature and is stirred for 1 h. 3.25 g (27.3 mmol) of benzotriazole are then added and a solution of 1.98 g (13.6 mmol) of glyoxal (40% in water) in 20 ml of methanol is added. After 2 h of stirring at ambient temperature, 1.03 g (27.3 mmol) of NaBH$_4$ are added in small portions. After 2 h of stirring, the methanol is evaporated and 2 g of KOH pellets are added. The solution is then extracted with three 100 ml portions of chloroform. After drying over MgSO$_4$ and evaporation of the solvents, (IIa) is isolated in the form of a yellow oil which crystallizes (0.4 g; yield=30%).

EXAMPLE 3

Synthesis of 8b-methyldecahydro-2a,4a,6a,8a-tetraazacyclopenta[fg]acenaphthylene [compound of the formula (IIb); series of steps (II); steps (C$_1$) and (C$_2$)]

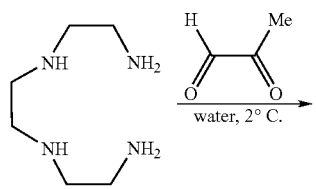

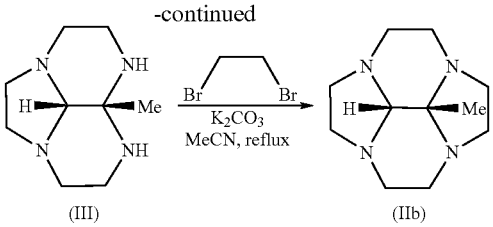

Synthesis of the Compound of the Formula (III) [Step (C$_1$)]

A solution of 1.23 g (6.8 mmol) of pyruvaldehyde (40% in water) in 10 ml of water is added by slow dropwise addition INto a solution of 1.00 g (6.8 mmol) of triethylenetetraamine in 40 ml of distilled water cooled to 2° C. On completion of addition, the reaction mixture is kept at 2° C. for 2 h. The water is then evaporated under reduced pressure and the compound (III) is obtained in the form of an orange oil which is used without purification for the synthesis of compound (IIb) (1.25 g).

Synthesis of the Compound of the Formula (IIb) [Step (C$_2$)]

A solution of 1.25 g (6.8 mmol) of compound (III) and of 3.79 g (27.4 mmol) of potassium carbonate (K$_2$CO$_3$) in 20 ml is acetonitrile is adjusted to 60° C. A solution of 1.38 g (6.8 mmol) of 1,2-dibromoethane in 10 ml of acetonitrile is then added. The mixture is stirred at 60° C. for 2 days. After filtration and evaporation of the solvents, the residue is redissolved in 20 ml of water and extracted with three 100 ml portions of chloroform. After drying over MgSO$_4$ and evaporation of the solvents, (IIb) is isolated in the form of an orange oil (0.42 g; yield=30%).

$^{13}$C NMR (125 MHz, CDCl$_3$, δ in ppm): 17.9; 47.7; 48.9; 49.3; 51.7; 75.8; 82.1.

EXAMPLE 4

Synthesis of 8b-methyldecahydro-2a,4a,6a,8a-tetraazacyclopenta[fg]acenaphthylene [compound of the formula (IIb); series of steps (II); step (C)]

A 40% strength solution of 61.53 g of pyruvaldehyde in water (341.8 mmol) in 20 ml of water is added by slow dropwise addition INto a solution of 50 g (341.8 mmol) of triethylenetetraamine in 800 ml of distilled water cooled to 2° C. On completion of addition, the reaction mixture is adjusted to ambient temperature and 81.36 g (683.6 mmol) of benzotriazole are added in a single portion. A solution of glyoxal (40% in water) (341.8 mmol) in 200 ml of methanol is then added by slow dropwise addition. After 2 h of stirring at ambient temperature, 25.85 g (683.6 mmol) of NaBH$_4$ are added in small portions. After 2 h of stirring at ambient temperature, the methanol is evaporated and 50 g of KOH pellets are added to the residue. The solution is then extracted with three 1.5 l portions of chloroform. After drying over MgSO$_4$ and evaporation of the solvents, (IIb) is isolated in the form of an orange oil (28.50 g; yield=40%).

EXAMPLE 5

Synthesis of 8b-methyldecahydro-2a,4a,6a,8a-tetraazacyclopenta[fg]acenaphthylene [compound of the formula (IIb); series of steps (II); step (C)]

A 40% strength solution of 61.56 g of pyruvaldehyde in water (342 mmol) in 100 ml of water is added by slow dropwise addition INto a solution of 60.66 g (342 mmol) of triethylenetetraamine hydrate (containing 17% water) in 300 ml of distilled water cooled to 2° C. On completion of addition, the reaction mixture is adjusted to ambient temperature and 81.40 g (684 mmol) of benzotriazole are added in a single portion. 300 ml of ethanol are then added to the reaction medium, then a solution of 49.59 g of glyoxal (40% in water) (342 mmol) in 100 ml of ethanol is added by slow dropwise addition. After 2 h of stirring at ambient temperature, the solution is cooled to 0° C. and 25.87 g (684 mmol) of $NaBH_4$ are added in small portions. After returning to ambient temperature, the reaction medium is stirred for 2 h, the ethanol is evaporated and 70 g of KOH pellets are added to the residue. The solution is then extracted with two 1 l portions of chloroform. After drying over $MgSO_4$ and evaporation of the solvents, (IIb) is isolated in the form of an orange oil (32.3 g; yield=45%).

EXAMPLE 6

Synthesis of 8b-methyldecahydro-2a,4a,6a,8a-tetraazacyclopenta[fg]acenaphthylene [compound of the formula (IIb): series of steps (II); step (C)]

A 40% strength solution of 6.16 g of pyruvaldehyde in water (34.2 mmol) in 10 ml of ethanol is added by slow dropwise addition into a solution of 5 g (34.2 mmol) of triethylenetetraamine in 30 ml of ethanol cooled to 0° C. On completion of addition, the reaction mixture is adjusted to ambient temperature and 8.15 g (68.5 mmol) of benzotriazole are added in a single portion. A solution of 4.97 g of glyoxal (40% in water) (34.2 mmol) in 5 ml of ethanol is added by slow dropwise addition. After 2 h of stirring at ambient temperature, the solution is cooled to 0° C. and 2.59 g (68.5 mmol) of $NaBH_4$ are added in small portions. After returning to ambient temperature, the reaction medium is stirred for 2 hours, the ethanol is evaporated, 50 ml of water and 6.5 g of KOH pellets are added to the residue. The solution is then extracted with two 300 ml portions of chloroform. After drying over $MgSO_4$ and evaporation of the solvents, (IIb) (a mixture of several isomers) is isolated in the form of an orange oil (4.84 g; yield=68%).

EXAMPLE 7

Synthesis of syclene [compound of the formula (I): series of steps (II); step (D)]

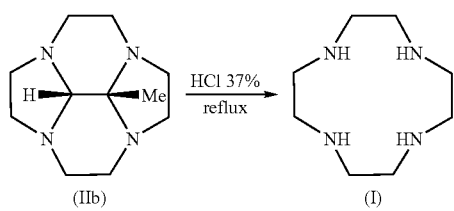

1.00 g of compound (IIb) prepared according to Example 4 is placed in 20 ml 37% strength HCl. The mixture is heated at reflux for 12 h. After cooling and filtration, the tetrachlorohydrate of compound (I), is isolated in the form a white powder (0.75 g; yield=50%).

$^{13}$C NMR (125 MHz, $D_2O$, δ in ppm): 44.6.

EXAMPLE 8

Synthesis of cyclene [compound of the formula (I); series of steps (II); steps (C)+(D) "in one pot"]

A 40% strength solution of 555 g of pyruvaldehyde in water (3.1 mol) in 500 ml of water is added by slow dropwise addition into a solution of 581 g (3.1 mol) of hydrated triethylenetetraamine (containing 22% water) in 3.5 l of distilled water cooled to 2° C. On completion of addition, the reaction mixture is adjusted to ambient temperature and stirred for two hours. 739 g (6.2 mol) of benzotriazole in 3.5 l of ethanol are added in a single portion, then a solution of 450 g of glyoxal (40% in water) (3.1 mol) is added by slow dropwise addition. After 12 h of stirring at ambient temperature, the solution is cooled to 0° C. and 235 g (6.2 mol) of $NaBH_4$ are added in small portions. After returning to ambient temperature, the reaction medium is stirred for 2 h. The precipitate which has formed is filtered and the volume of the reaction medium is reduced to 3 l. After chloroform extraction, drying over magnesium sulfate and evaporation of the solvents, (IIb) is isolated in the form of an orange oil which is placed in 4 l of 37% strength HCl. The mixture is heated to 80° C. for 12 h. After cooling and filtration, the tetrachlorohydrate of compound (I) is isolated in the form a white powder (147 g; yield=15%).

EXAMPLE 9

Synthesis of a mixture of isomers (IVa)+(IVa') [compounds in which R'=—$CH_2$—$C_6H_5$ and X=Br)

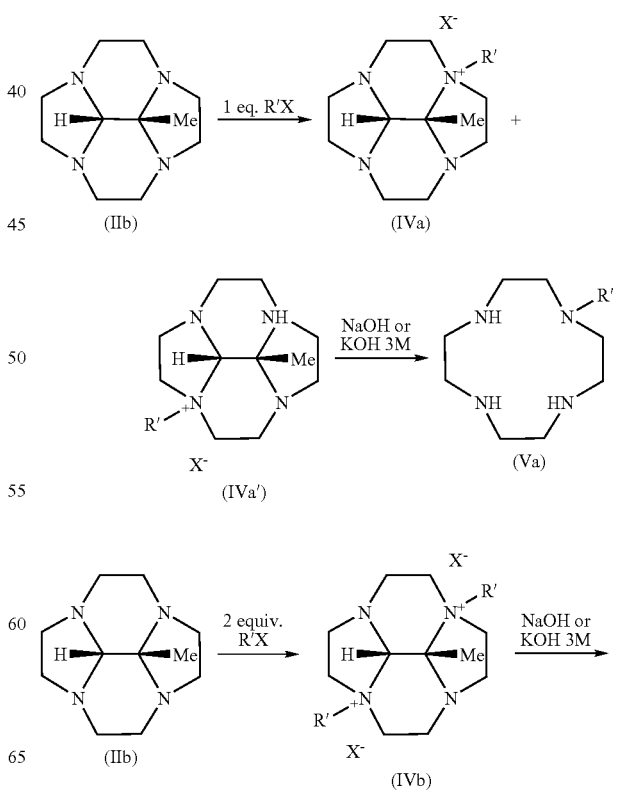

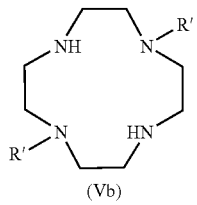

(Vb)

0.66 g (3.86 mmol) of benzyl bromide is added to a solution of 1.01 g (4.86 mmol) of compound (IIb) in 4 ml of toluene. After 24 hours of stirring at ambient temperature, the solid which has formed is filtered, washed with ether and then dried. The mixture of the two isomers (IVa) and (IVa') (R'=—$CH_2$—$C_6H_5$, X=Br) is isolated in the form of a yellow powder (1.24 g; yield=84%).

$^{13}C$ NMR (125 MHz, DMSO-$d^6$, δ in ppm): 12.0; 25.0; 43.0; 44.8; 45.0; 45.4; 47.9; 48.3; 48.6; 49.2; 49.5; 49.6; 50.6; 52.5; 56.7; 58.6; 59.3; 61.1; 62.8; 76.4; 77.7; 87.5; 87.9; 126.3; 129.2; 129.5; 129.9; 130.1; 131.1; 131.3; 133.2; 134.2.

EXAMPLE 10

Synthesis of a mixture of isomers (IVa)+(IVa') [compounds in which R'=—$CH_2$—$C_6H_4$-pCH=$CH_2$ and X=I]

0.62 g (4.07 mmol) of 4-vinylbenzyl chloride is added into a solution of 1.06 g (5.10 mmol) of compound (IIb) and 0.61 g (4.07 mmol) of sodium iodide in 6 ml of acetonitrile. After 24 hours of stirring at ambient temperature, the solid which has formed is filtered, washed with ether and then dried. The mixture of the two isomers (IVa) and (IVa') (R'=—$CH_2$—$C_6H_4$-pCH=$CH_2$, X=I) is isolated in the form of a yellow powder (0.92 g) containing sodium chloride.

$^{13}C$ NMR (125 MHz, DMSO-$d^6$, δ in ppm): 12.1; 25.2; 43.0; 44.7; 45.1; 45.5; 47.9; 48.3; 48.6; 49.3; 49.5; 49.7; 50.4; 52.5; 56.8; 58.4; 59.4; 61.1; 62.4; 76.5; 77.7; 87.3; 88.0; 117.2; 127.5; 127.8; 128.9; 129.3; 133.5; 134.5; 136.8; 139.7; 139.9.

EXAMPLE 11

Synthesis of a mixture of isomers (IVa)+(IVa') [compounds in which R'=—$CH_2CONH_2$ and X=I)]

0.36 g (1.95 mmol) of iodoacetamide is added into a solution of 0.51 g (2.45 mmol) of compound (IIb) in 6 ml of tetrahydrofuran. After 24 hours of stirring at ambient temperature, the solid which has formed is filtered, washed with ether and then dried. The mixture of the two isomers (IVa) and (IVa') (R'=—$CH_2CONH_2$, X=I) is isolated in the form of an orange powder (0.46 g; yield=60%).

$^{13}C$ NMR (125 MHz, $D_2O$, δ in ppm): 11.2; 21.5; 25.7; 41.0; 43.9; 44.7; 45.5; 46.3; 47.0; 47.7; 47.9; 48.4; 49.3; 50.6; 56.7; 58.6; 60.2; 62.0; 65.0; 68.3; 75.9; 77.6; 89.1; 157.0.

EXAMPLE 12

Synthesis of a compound (IVb) [compound in which R'=—$CH_2$—$C_6H_5$ and X=I]

1.21 g (7.07 mmol) of benzyl bromide are added without precautions into a solution of 0.49 g (2.36 mmol) of compound (IIb) and 0.92 g (7.07 mmol) of sodium iodide in 10 ml of acetonitrile. After 24 hours of stirring at ambient temperature, the precipitate obtained is filtered, washed with ether and then dried. The compound (IVb) (R'=—$CH_2$—$C_6H_5$, X=I) is isolated in the form of a yellow-orange powder (1.33 g) containing sodium bromide.

$^{13}C$ NMR (125 MHz, DMSO-$d^6$; δ in ppm): 15.7; 42.4; 45.5; 46.2; 55.3; 55.7; 58.5; 59.0; 61.2; 62.4; 84.7; 86.8; 129.4; 129.5; 130.0; 130.4; 131.5; 131.6; 133.3; 134.4.

EXAMPLE 13

Synthesis of a compound (Va) in which R'=—$CH_2$—$C_6H_5$

A solution of 1.10 g (2.90 mmol) of the mixture of isomers (IVa)+(IVa') (R'=—$CH_2$—$C_6H_5$, X=Br) prepared according to Example 8 in 50 ml of a 3M aqueous solution of potassium hydroxide is heated to 80° C. for 16 hours. The solution is extracted with three 30 ml portions of chloroform. After drying over $MgSO_4$ and evaporation of the solvents, the compound (Va) (R'=—$CH_2$—$C_6H_5$) is obtained in the form of an oil (0.54 g, yield=72%).

$^{13}C$ NMR (125 MHz, $CDCl_3$, δ in ppm): 45.7; 46.8; 47.8; 51.8; 59.8; 127.5; 128.8; 129.5, 139.4.

EXAMPLE 14

Synthesis of the compound (Va) in which R'=—$CH_2$—$C_6H_4$—CH=$CH_2$

A solution of 0.92 g of the mixture of isomers (IVa)+(IVa') (R'=—$CH_2$—$C_6H_4$—CH=$CH_2$, X=I) containing sodium chloride, prepared according to Example 9, in 20 ml of a 2M aqueous solution of potassium hydroxide is stirred at ambient temperature for 72 h. The solution is extracted with three 20 ml portions of chloroform. After drying over $MgSO_4$ and evaporation of the solvents, the compound (Va) (R'=—$CH_2$—$C_6H_4$—CH=$CH_2$) is obtained in the form of a yellow oil (0.40 g, overall yield relative to the 4-vinylbenzyl chloride=34%).

$^{13}C$ NMR (125 MHz, $CDCl_3$, δ in ppm): 45.5; 46.8; 47.6; 52.0; 59.4; 113.8; 126.8; 129.7; 136.9; 137.2; 139.2.

EXAMPLE 15

Synthesis of the compound (Vb) in which R'=—$CH_2$—$C_6H_5$

A solution of 1.9 g of compound (IVb) (R'=—$CH_2$—$C_6H_5$, X=I) containing sodium bromide, prepared according to Example 11, in 50 ml of a 3M sodium hydroxide solution is heated at reflux for 12 h. The solution is extracted with three 100 ml portions of chloroform. After drying over $MgSO_4$ and evaporation of the solvents, the compound (Vb) (R'=—$CH_2$—$C_6H_5$) is obtained in the form of a yellow oil (0.45 g, overall yield relative to the compound (IIb)=27%).

$^{13}C$ NMR (125 MHz, $CDCl_3$, δ in ppm): 45.9; 52.6; 60.6; 127.8; 129.0; 129.7; 139.8.

EXAMPLE 16

Synthesis of the compound (VI) in which R'= —CH$_2$—C$_6$H$_5$

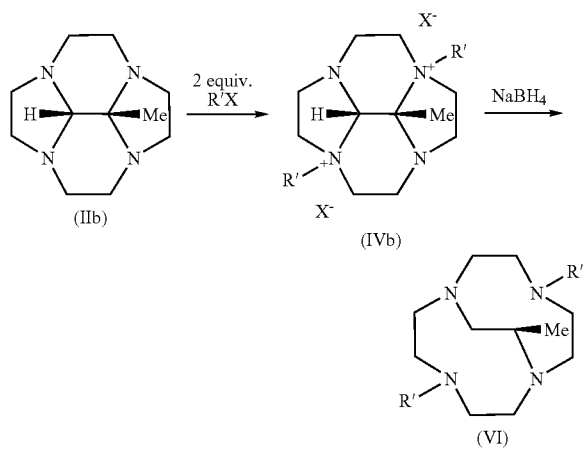

A solution of 0.75 g (1.16 mmol) of the compound (IVb) (R'=—CH$_2$—C$_6$H$_5$, X=I) containing sodium bromide, prepared according to Example 11, in 25 ml of absolute ethanol is adjusted to 0° C. and 1.10 g (29.1 mmol) of sodium borohydride are added slowly. After 24 hours of stirring at ambient temperature, the excess sodium borohydride is eliminated by addition of 6 ml of a 37% strength solution of hydrochloric acid. The various solvents are evaporated, then the solid obtained is redissolved in 20 ml of water. The solution is extracted with three 10 ml portions of dichloromethane. After drying over MgSO$_4$ and evaporation of the solvents, the compound (VI) (R'=—CH$_2$—C$_6$H$_5$) is obtained in the form of a yellow solid (0.23 g; overall yield relative to the compound (IIb)=41%).

$^{13}$C NMR (125 MHz, CDCl$_3$, δ in ppm): 13.3; 49.0; 49.5; 50.8; 52.8; 53.5; 54.3; 55.1; 55.7; 57.0; 60.0; 60.4; 128.3; 128.4; 129.6; 129.9; 130.2; 137.9; 138.2.

The compound (VII) may be obtained by hydrogenolysis of the compound of the formula (VI) in which R' is a benzyl residue.

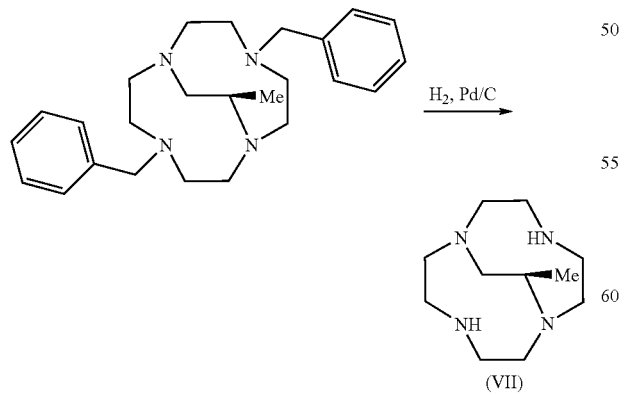

The method for synthesizing decahydro-2a,4a,6a,8a-tetraazacyclopenta[fg]acenaphthylene (IIa) from triethylenetetraamine [step (A)] is an advantageous alternative to previously known methods for preparing this cyclene precursor.

Indeed, unlike all previously described methods, it is a one pot method which does not require isolation of the intermediate, non-cyclized bisaminal derivative. The use of toxic dihalogenated derivatives (dibromo- or dichloroethane) is avoided. A recent method also permits the avoidance of such derivatives, but requires three steps, one of which is a delicate reduction reaction of a diamide intermediate. Finally, the reaction conditions, ambient temperature, concentrated water/methanol medium, very short reaction times, are suited to an industrial synthesis method for decahydro-2a,4a,6a,8a-tetraazacyclopenta[fg]acenaphthylene (IIa).

The method for synthesis of cyclene via the intermediate (IIb) described in this invention [series of steps (II)] exhibits the same advantages as those previously mentioned for the synthesis of compound (IIa). In addition, step (D) is easier to carry out than step (B). In fact, treating (IIb) with a 37% strength solution of HCl is sufficient to obtain cyclene with a yield of 50%, so making it possible to avoid the use of reagents such as hydroxylamine in excess or alternatively oxidizing agents (Br$_2$, KMnO$_4$) and/or severe conditions (autoclave at 180° C., heating a concentrated H$_2$SO$_4$ solution at reflux).

The aminal bridge has already been used as a protective group for selectively functionalizing one or two amine functions in trans position of a cyclic tetraamine[23-30] or in order to gain access to macrobicyclic derivatives of cyclene or cyclam.[31-39] However, the derivatives of the bisaminal type are obtained by the action of formaldehyde or glyoxal on the already formed macrocycle. In this invention, 8b-methyl-decahydro-2a,4a,6a,8a-tetraazacyclopenta[fg]acenaphthylene (IIb) may be selectively mono- or diquaternized in order to give rise, after basic hydrolysis, to N-mono- or 1,7-difunctionalized cyclenes. The conditions for deprotecting the compounds of the formulae (IVa), (IVa') and (IVb) are milder than those necessary for hydrolyzing the non-methylated analogues obtained by using glyoxal. The tri-N-functionalized cyclenes may readily be obtained by functionalization of the mono-N-benzylated cyclene followed by a hydrogenolysis reaction. Difunctional chelating agents, very high value-added macrocycles, some of which are used as MRI contrast media, may be prepared equally well from mono or tri N-functionalized cyclenes.

This method therefore provides direct access to precursors of difunctional chelating agents starting directly from the linear amine, the same bisaminal group simultaneously acting as a "template" promoting the cyclization reaction and as a protective group enabling selective functionalization. This novel method thus makes it possible to prepare, in a limited number of steps, very high value-added macrocycles which are used in medical applications, in particular as contrast media for medical imaging. Finally, it should be noted that reduction of the diquaternized intermediates gives rise to novel macrobicyclic ligands, methylated analogues of compounds which are already the subject matter of several patents.

The references for the publications cited in the present specification are as follows:
  (1) Athey, P. S.; Kiefer, G. E., WO 95/14726; Athey, P. S.; Kiefer, G. E. *J. Org. Chem.* 2002, 67, 4081-4085.
  (2) Sandnes, R. W.; Vasilevskis, I.; Undheim, K.; Gacek, M., WO 96/28432,
  (3) Schultze, L.; Bulls, A. R., WO 96/28433,
  (4) Argese, M.; Ripa, G.; Scala, A.; Valle, V., WO 97/49691, (5) Petrov, O.; Prelle, A.; Graske, K.; Nickisch, K.; Raduchel, B.; Platzek, I., WO 97/31905,
(6) Argese, M.; Ripa, G.; Scala, A.; Valle, V., WO 98/45296,
(7) Hervé, G.; Bernard, H.; Le Bris, N.; Yaouanc, J. J.; Handel, H. *Tetrahedron Lett.* 1998, 39, 6861-6864.
(8) Ripa, G.; Argese, M., WO 98/49151,
(9) Sandnes, R. W.; Gacek, M.; Undheim, K. *Acta Chem. Scand.* 1998, 52, 1402-1404.
(10) Argese, M.; Ripa, G., WO 99/05145,
(11) Hervé, G.; Bernard, H.; Le Bris, N.; Le Baccon, M.; Yaouanc, J. 1; Handel, H. *Tetrahedron Lett.* 1999, 40, 2517-2520,
(12) Argese, M.; Manfredi, G.; Rebasti, F.; Ripa, G., WO 00/53588,
(13) Ferrari, M.; Giovenzana, G. B.; Palmisano, G.; Sisti, M. *Synth. Commun.* 2000, 30, 15-21,
(14) Hervé, G.; Bernard, H.; Toupet, L.; Handel, H. *Eur. J. Org. Chem.* 2000, 33-35,
(15) Platzek, J.; Hoyer, K.; Graske, K.-D.; Radüchel, B., WO 00/32581,
(16) Vasilevskis, J.; Varadarajan, J.; Garrity, M.; Fellmann, J. D.; Messerle, L.; Amarasinghe, C., U.S. Pat. No. 6,048,979,
(17) Argese, M.; Brocchetta, M.; Manfredi, G.; Rebasti, F.; Ripa, G.; WO 2001-79207
(18) Tripier, R.; Denat, F.; Guilard, R.; Ledon, H., FR 2 810 035,
(19) Liu, S.; Edwards, D. S. *Bioconjugate Chem.* 2001, 7-34.
(20) Denat, F.; Brandès, S.; Guilard, R. *Synlett,* 2000, 561-574.
(21) Jacques, V.; Desreux, J.-F. in *Chemistry of Contrast Agents in Medical Magnetic Resonance Imaging* 2001, 157-191.
(22) Richman, J. E.; Atkins, T. J. *J. Am. Chem. Soc.* 1974, 96, 2268-2270.
(23) Royal, G.; Dahaoui-Gindrey, V.; Dahaoui, S.; Tabard, A.; Guilard, R.; Pullumbi, P.; Lecomte, C. *Eur. J. Org. Chem.* 1998, 1971-1975.
(24) Bucher, C.; Royal, G.; Barbe, J.-M.; Guilard, R. *Tetrahedron Lett.* 1999, 40, 2315-2318.
(25) Bucher, C.; Duval, E.; Barbe, J. M.; Verpeaux, J. N.; Amatore, C.; Guilard, R. *C. R. Acad. Sci. Ser. II,* 2000, 3, 211-222.
(26) Kotek, J.; Hermann, P.; Vojtisek, P.; Rohovec, J.; Lukes, I. *Collect. Czech. Chem. Comm.* 2000, 65, 243-266.
(27) Rohovec, J.; Gyepes, R.; Cisarova, I.; Rudovsky, J.; Lukes, I. *Tetrahedron Lett.* 2000, 41, 1249-1253.
(28) Kurosaki, H.; Bucher, C.; Espinosa, E.; Barbe, J.-M.; Guilard, R. *Inorg. Chim. Acta* 2001, 322, 145-149.
(29) Le Baccon, M.; Chuburu, F.; Toupet, L.; Handel, H; Soibinet, M.; Dechamps-Olivier, L; Barbier, J.-P.; Aplincourt, M. *New J. Chem.* 2001, 25, 1168-1174.
(30) Boschetti, F.; Denat, F.; Espinosa, E.; Guilard, R. *Chem. Commun.* 2002, 312-313.
(31) Weisman, G. R.; Rogers, M. E.; Wong, E. W.; Jasinski, J. P.; Paight, E. S. *J. Am. Chem. Soc.* 1990, 112, 8604-8605.
(32) Weisman, G. R.; Wong, E. H.; Hill, D. C.; Rogers, M. E.; Reed, D. P.; Calabrese, J. C. *Chem. Commun.* 1996, 947-948.
(33) Hiler, G. D., II; Perkins, C. M., WO 98/39335
(34) Hiler, G. D., II; Perkins, C. M., WO 00/32601,
(35) Wong, E. H.; Weisman, G. R.; Hill, D. C.; Reed, D. P.; Rogers, M. E.; Condon, J. S.; Fagan, M. A.; Calabrese, J. C.; Lam, K. C.; Guzei, I. A.; Rheingold, A. L. *J. Am. Chem. Soc.* 2000, 122, 10561-10572.
(36) Nestler, B.; Seebach, M., EP 0 940 402,
(37) Perkins, C. M., WO 2002-26748,
(38) Perkins, C. M.; Kitko, D. I, WO 2002-26267,
(39) Hubin, T. J.; Meade, T. J., WO 2002-06287.

The invention claimed is:

1. A method of preparing a cyclene of formula (I):

from ethylenediamine of formula (VIII'):

comprising the steps of:

preparing in one pot the compound of formula (IIa),

from the compound of formula (VIII') by the reaction of glyoxal and benzotriazole; and transforming the compound of formula (IIa) into the cyclene of formula (I), wherein said preparation step is carried out without using dibromoethane or dichloroethane.

2. A method of preparing N-monofunctionalized cyclene derivatives of formula (Va):

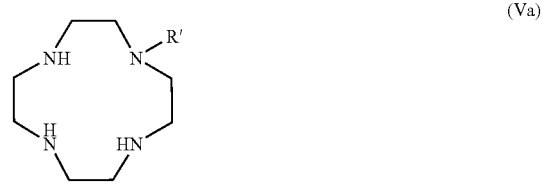

and $N_1$, $N_7$-difunctionalized cyclene derivatives of formula (Vb):

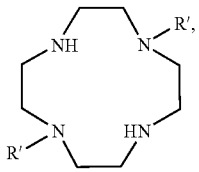
(Vb)

comprising the steps of:
reacting a compound of formula (IX):
R'X(IX), in which X represents a halogen atom, with a compound of formula (IIb):

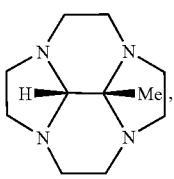
(IIb)

to form, depending on the stoichiometry of the reaction, a mixture of compounds of formulae (IVa) and (IV'a):

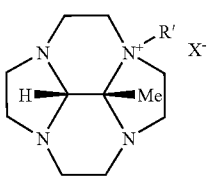
(IVa)

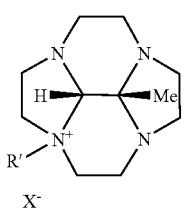
(IV'a)

or a compound of formula (IVb):

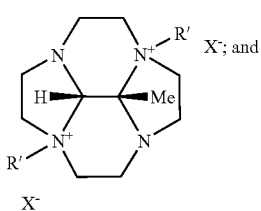
(IVb)

subjecting the mixture of compounds of formulae (IVa) and (IV'a) or the compound of formula (IVb) to alkaline hydrolysis to form, respectively, the compound of formula (Va) or (Vb), wherein, R' in the formulae (Va), (Vb), (IVa), (IVb), and (IX) is an alkyl residue, which is linear or branched, comprising from 1 to 15 carbon atoms and a $-(CH_2)_w-Y$ residue, in which w represents a number greater than zero and less than or equal to 6, and Y is selected from the group consisting of:

an aromatic cycle comprising from 6 to 14 carbon atoms, the aromatic cycle is optionally substituted in ortho and/or meta and/or para positions by a substituent group selected from the group consisting of (i) a halogen atom, (ii) an alkyl group comprising from 1 to 4 carbon atoms, (iii) an OH residue, (iv) an $OR^1$ residue in which $R^1$ represents an alkyl residue comprising from 1 to 4 carbon atoms, an aryl residue or an aromatic heterocycle, (v) a nitro group (vi) an $NH_2$, $-(C=O)NH_2$, $NHR^2$, $-(C=O)NHR^2$, $NR^2R^3$ or $-(C=O)NR^2R^3$ group, in which $R^2$ and $R^3$, identical or different, mutually independently represent an alkyl residue selected from among methyl, ethyl, propyl, isopropyl, n-butyl, isobutyl, sec-butyl or tert-butyl residues, an aromatic heterocycle, the aromatic heterocycle is optionally substituted in ortho and/or meta and/or para positions by a substituent selected from the group consisting of (i) a halogen atom, (ii) an alkyl group comprising from 1 to 4 carbon atoms, (iii) an OH residue, (iv) an $OR^1$ residue in which $R^1$ represents an alkyl residue comprising from 1 to 4 carbon atoms, an aryl residue or an aromatic heterocycle, (v) a nitro group (vi) an $NH_2$, $-(C=O)NH_2$, $NHR^2$, $-(C=O)NHR^2$, $NR^2R^3$ or $-(C=O)NR^2R^3$ group, in which $R^2$ and $R^3$, identical or different, mutually independently represent an alkyl residue selected from among methyl, ethyl, propyl, isopropyl, n-butyl, isobutyl, sec-butyl or tert-butyl residues, and a residue selected from the group consisting of cyano, $PO_3H_2$, $SO_3H$, $NH_2$, $-(C=O)NH_2$, $NHR^2$, $-(C=O)NHR^2$, $NR^2R^3$ or $-(C=O)NR^2R^3$ residues, in which $R^2$ and $R^3$, identical or different, mutually independently represent a methyl, ethyl, propyl, isopropyl, n-butyl, isobutyl, sec-butyl or tert-butyl residues or a $CO_2R^4$ residue, in which $R^4$ represents a hydrogen atom, an alkyl residue comprising from 1 to 4 carbon atoms.

3. A method of preparing N-monofunctionalized cyclene derivatives of formula (Va):

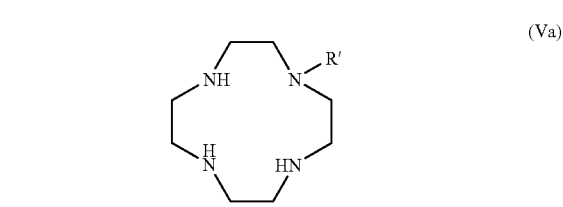
(Va)

and $N_1, N_7$-difunctionalized cyclene derivatives of formula (Vb):

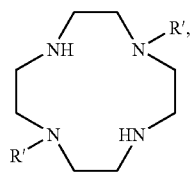

comprising the steps of:
reacting a compound of formula (IX):
R'X(IX), in which X represents a halogen atom, with a compound of formula (IIb):

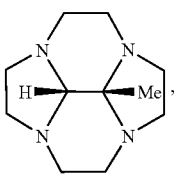

to form, depending on the stoichiometry of the reaction, a mixture of compounds of formulae (IVa) and (IV'a):

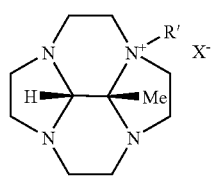

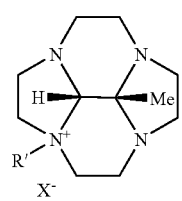

or a compound of formula (IVb):

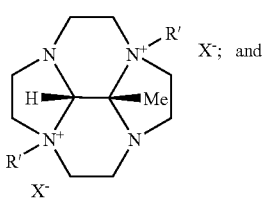

subjecting the mixture of compounds of formulae (IVa) and (IV'a) or the compound of formula (IVb) to alkaline hydrolysis to form, respectively, the compound of formula (Va) or (Vb), wherein, R' in the formulae (Va), (Vb), (IVa), (IVb), and (IX) is an alkyl residue, which is linear or branched, comprising from 1 to 15 carbon atoms and a $-(CH_2)_w-Y$ residue, in which w represents a number greater than zero and less than or equal to 6, and Y is an optionally substituted aromatic heterocycle comprising from one to 3 nitrogen atoms, from 4 to 12 carbon atoms.

4. A method of preparing N-monofunctionalized cyclene derivatives of formula (Va):

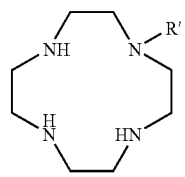

and $N_1, N_7$-difunctionalized cyclene derivatives of formula (Vb):

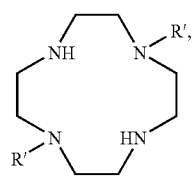

comprising the steps of:
reacting a compound of formula (IX):
R'X(IX), in which X represents a halogen atom, with a compound of formula (IIb):

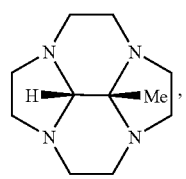

to form, depending on the stoichiometry of the reaction, a mixture of compounds of formulae (IVa) and (IV'a):

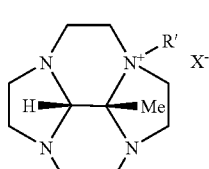

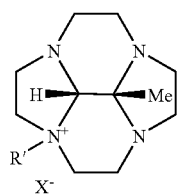
(IV'a)

or a compound of formula (IVb):

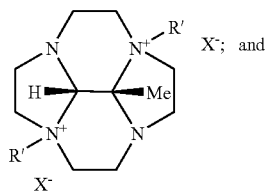
(IVb)

subjecting the mixture of compounds of formulae (IVa) and (IV'a) or the compound of formula (IVb) to alkaline hydrolysis to form, respectively, the compound of formula (Va) or (Vb), wherein, R' in the formulae (Va), (Vb), (IVa), (IVb), and (IX) is an alkyl residue, which is linear or branched, comprising from 1 to 15 carbon atoms and a —$(CH_2)_w$—Y residue, in which w represents a number greater than zero and less than or equal to 6, and Y is a $CO_2R^4$ residue, in which $R^4$ represents a phenyl residue.

5. A method of preparing a cyclene of formula (I):

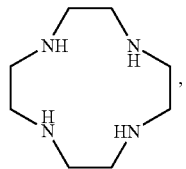
(I)

from triethylenetetraamine of formula (VIII):

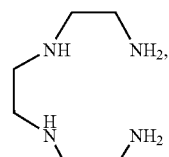
(VIII)

comprising the steps of:

preparing a one pot preparation of the compound of formula (IIa):

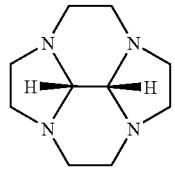
(IIa)

by the reaction of the compound of formula (VIII) with glyoxal and benzotriazole; and transforming the compound of formula (IIa) into the cyclene of formula (I), wherein said preparation step is carried out without using dibromoethane or dichloroethane.

* * * * *